(12) United States Patent
Burkart et al.

(10) Patent No.: US 6,281,392 B1
(45) Date of Patent: Aug. 28, 2001

(54) PREPARATION OF ORTHOESTERS

(75) Inventors: Kirsten Burkart, Ludwigshafen; Josef Guth, Freinsheim; Thomas Letzelter, Annweiler; Jürgen Schweinzer, Frankenthal; Hans-Josef Sterzel, Dannstadt-Schauernheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/440,052

(22) Filed: Nov. 15, 1999

(30) Foreign Application Priority Data

Nov. 18, 1998 (DE) .............................................. 198 53 089

(51) Int. Cl.⁷ ..................................................... C07L 43/30
(52) U.S. Cl. ........................... 568/595; 568/591; 568/592
(58) Field of Search .................................... 568/591, 592, 568/595

(56) References Cited

U.S. PATENT DOCUMENTS

| 3,274,261 | 9/1966 | Lenz et al. | 260/615 |
|---|---|---|---|
| 3,901,946 | 8/1975 | Lenz et al. | 260/615 |

FOREIGN PATENT DOCUMENTS

| 1068103 | 7/1992 | (CN) . |
|---|---|---|
| 1106375 | 9/1994 | (CN) . |
| 919465 | 10/1954 | (DE) . |
| 36 06 472 | 9/1987 | (DE) . |
| 3606472 | 9/1987 | (DE) . |
| 59001435 | 2/1982 | (JP) . |
| 58225036 | 6/1982 | (JP) . |
| 125 872 | 5/1984 | (PL) . |
| 125872 | 5/1984 | (PL) . |
| 1671656 | 9/1989 | (RU) . |
| 1781203 | 3/1990 | (RU) . |
| 178 1203 | 12/1992 | (RU) . |
| 2072978 | 3/1993 | (RU) . |

OTHER PUBLICATIONS

"Organic Syntheses, Collective Bolum I, Second Edition" (1946), Wiley, New York XP002131065 pp. 258–261.
Abstract SU 207 2978, Mar. 11, 1993.
Abstract CN 1068103, Jul. 1, 1992.
Abstract JP 58225 036, Jun. 24, 1982.
Abstract CN 1106375, Sep. 1, 1994.

*Primary Examiner*—Rosalynd Keys
(74) *Attorney, Agent, or Firm*—Keil & Weinkauf

(57) ABSTRACT

Orthoesters are prepared by reacting 1,1,1-trihaloalkanes with alkali metal alkoxides in the presence of the corresponding alcohol, a slurry of the alkali metal alkoxide in the corresponding alcohol being used.

9 Claims, No Drawings

PREPARATION OF ORTHOESTERS

The present invention relates to a process for preparing orthoesters by reacting metal alkoxides with 1,1,1-trihaloalkanes. Orthoesters, in particular trialkylorthoesters and, among these, particularly the trialkylorthoesters of formic acid ("orthoformates"), are important synthesis building blocks in organic chemistry and are used, for example, to prepare usually complex organic structures such as pharmaceuticals or plant protection agents. The orthoesters of most economic importance are the two orthoformates trimethyl orthoformate ("TMOF") and triethyl orthoformate ("TEOF").

Processes for preparing orthoesters from metal alkoxides and 1,1,1-trihaloalkanes have long been known. Usually, for this purpose, three moles of a metal alkoxide MOR (M=metal, R=organic radical) are reacted with a 1,1,1-trihaloalkane R'—$CHal_3$ (Hal=F, Cl, Br, I, R'=H or organic radical), the orthoester R'—$C(OR)_3$ forming with the elimination of alkali metal halide. To prepare orthoformates, accordingly, alkali metal alkoxide MOR is reacted with trihalomethane H—$CHal_3$. Generally, when orthoesters are prepared, use is made of chlorine as halogen and of sodium as alkali metal, since these are the cheapest representatives of their groups. Therefore, for the industrial preparation of TMOF or TEOF, usually sodium methoxide (M=Na, R=$CH_3$) or sodium ethoxide (M=Na, R=$CH_2CH_3$) is reacted with chloroform (trichloromethane, R'=H, Hal=Cl).

Usually, the processes for preparing orthoesters are carried out in homogeneous solution (apart from alkali metal halide which precipitates out) with the corresponding alcohol as solvent; TMOF is therefore prepared in methanolic solution and TEOF in ethanolic solution. Frequently in this reaction, the alkali metal alkoxide, when a solution of alkali metal hydroxide in the alcohol is used, is not formed in equilibrium until before or during the reaction. Thus, DE-A 21 04 206 teaches a process for the continuous preparation of trialkyl orthoformates by reacting chloroform with a solution of an alkali metal alkoxide in the corresponding alcohol, the reaction being carried out in the absence of water and oxygen at from 40 to 120° C. and a pressure of from 1 to 8 bar. PL-B 125872 discloses the preparation of triethyl orthoformate by reacting chloroform with three moles of sodium ethoxide in ethanol. CN-A 1106375 discloses the preparation of triethyl orthoformate by slowly adding ethanol to a mixture of sodium hydroxide and chloroform, the pH of the reaction mixture being kept at from 7 to 10. JP-A 59-001 435 teaches preparing trialkyl orthoformates by reacting the alcohol, a solution of from 5 to 23% by weight of alkali metal hydroxide in the alcohol, and chloroform. DE-A 36 06 472 teaches a process for preparing trialkyl orthoformates by isothermic reaction of chloroform and an alcoholic solution of alkali metal alkoxide at from 1 to 6 bar, from 30 to 120° C. and a pH above 7, use being made of a stoichiometric excess of chloroform. The molar ratio of chloroform to the alkoxide is from 1 to 2:3.

These processes have the disadvantage that the alcoholic solvent must be separated off from the orthoester. When the orthoester is isolated from customary reaction mixtures, to achieve the orthoester product purity demanded by the market, distillation towers having a high number of theoretical plates and a correspondingly high energy consumption are required.

Therefore, attempts have been made with other processes to avoid the use of alcohol as solvent or at least to avoid distilling orthoester/alcohol mixtures.

Thus, DE-A 12 17 943 teaches reacting chloroform with a metal methoxide suspended in the trialkyl orthoformate to be prepared, a yield of 84 mol %, based on methoxide used, being achieved. JP-A 58-225 036 teaches extracting orthoesters from a mixture of alcohol, alkali metal hydroxide and chloroform with optionally halogen-substituted aliphatic or aromatic hydrocarbons or ethers. CN-A 10 68 103 teaches using an inert solvent in the reaction.

Other processes are carried out in the presence of a phase-transfer catalyst. RU-A 20 72 978 and SU-A 1781203 teach reacting an alkanol and an alkali metal hydroxide with chloroform in the presence of phase-transfer catalysts.

However, a characteristic of these known processes using heterogeneous reaction mixtures (not considering the alkali metal halide precipitating out) is the disadvantage of forming by-products in comparatively high amount; the selectivity of the reaction is unsatisfactory. The extraction processes, in addition to unsatisfactory selectivity of the reaction, usually have the disadvantage of an additional process step.

SU-A 16 71 656 teaches another process for preparing orthoesters by reacting chloroform with the corresponding tetraalkoxisilane in pseudocumene as solvent in the presence of alkali metal hydroxide and triethylbenzylammonium chloride. This process is unsatisfactory economically because of the use of comparatively expensive chemicals.

It is an object of the present invention, therefore, to find an economically satisfactory process for preparing orthoesters having high selectivity, high space-time yield and a low product purification requirement.

We have found that this object is achieved by a process for preparing orthoesters by reacting 1,1,1-trihaloalkanes with alkali metal alkoxides in the presence of the corresponding alcohol, which comprises using a slurry of the alkali metal alkoxide in the corresponding alcohol.

The process according to the invention avoids separating off large amounts of alcohol, and the expenditure for isolating the pure product is therefore substantially lower than with known processes. At the same time, despite the presence of solid alkali metal alkoxide in the reaction medium, surprisingly, no impairment in selectivity with respect to the use of a pure solution of the alkoxide in the alcohol occurs.

By means of the process according to the invention, orthoesters of the formula R'—$C(OR)_3$ are prepared by reacting an alkali metal alkoxide MOR with a 1,1,1-trihaloalkane R'—$CHal_3$. It is equally possible, using the process according to the invention, to prepare mixed orthoesters, that is those which do not bear the same three radicals R, but two or three different radicals, that is orthoesters of the formulae R'—$C(OR^1)_2(OR^2)$ or R'—$C(OR^1)(OR^2)(OR^3)$. $R^1$, $R^2$ and $R^3$ each independently of one another correspond to a radical R. To prepare them, the corresponding alkoxides $MOR^1$, $MOR^2$ and/or $MOR^3$ and the corresponding alcohols $HOR^1$, $HOR^2$ and/or $HOR^3$ must be used in the desired ratio.

M is alkali metal, that is to say lithium, sodium, potassium, rubidium and/or cesium. It is possible to use a single alkali metal or a mixture of various alkali metals. Preference is given to the use of sodium or potassium, particular preference is given to the use of sodium.

Hal is halogen, that is to say fluorine, chlorine, bromine and/or iodine. A single halogen or a mixture of halogens can be used. Preference is given to the use of chlorine.

R is an organic radical, such as alkyl, alkenyl, alkinyl, cycloalkyl, cycloalkenyl, aryl, alkaryl or aralkyl. The radical R can be substituted with further organic radicals and can also contain heteroatoms.

Examples of radicals R which are usable in the process according to the invention are unbranched saturated alkyls having from one to 18 carbons, such as methyl, ethyl, propyl, butyl, pentyl, hexyl, heptyl, octyl, nonyl or decyl, saturated cyclic alkyls having from three to 12 carbons, such as cyclopentyl, cyclohexyl or cycloheptyl, or branched saturated alkyls such as 2-propyl, 2-butyl, 2-methyl-1-propyl, 1,1-dimethylethyl or all branched isomeric pentyl, hexyl, heptyl, octyl, nonyl or decyl radicals. R can likewise be an aromatic radical, for example phenyl or 1- or 2-naphthyl. Preferably, R is an unbranched alkyl, in particular methyl, ethyl, 1-propyl or 1-butyl. Particularly preferably, R is methyl or ethyl.

R' is a hydrogen or an organic radical R as defined above.

Examples of organic radicals R' usable in the process according to the invention are unbranched saturated alkyls having from one to 18 carbons, such as methyl, ethyl, propyl, butyl, pentyl, hexyl, heptyl, octyl, nonyl or decyl, saturated cyclic alkyls having from three to 12 carbons, such as cyclopentyl, cyclohexyl or cycloheptyl, or branched saturated alkyls such as 2-propyl, 2-butyl, 2-methyl-1-propyl, 1,1-dimethylethyl or all branched isomeric pentyl, hexyl, heptyl, octyl, nonyl or decyl radicals. R' can likewise be an aromatic radical, for example phenyl or 1- or 2-naphthyl (the 1,1,1-trihaloalkane is then an aromatically substituted 1,1,1-trihalomethane). Preferably, R' is hydrogen or an unbranched alkyl, in particular methyl, ethyl, 1-propyl or 1-butyl. Particularly preferably, R' is hydrogen, methyl or ethyl.

In the particularly preferred embodiments of the process according to the invention, either TMOF is prepared by reacting sodium methoxide (R=methyl, M=Na) with chloroform (R'=H, Hal=Cl), or TEOF is prepared by reacting sodium ethoxide (R=ethyl, M=Na) with chloroform (R'=H, Hal=Cl).

The alkali metal alkoxides are prepared in a known manner, for example by reacting alkali metal hydroxide with the alcohol, dissolving the alkali metal in the corresponding alcohol or decomposing the alkali metal amalgam formed in the amalgam process for chlor alkali electrolysis using the corresponding alcohol. The alkali metal alkoxides are also commercially available as customary goods.

The alkali metal alkoxide MO—R is slurried in the process according to the invention with the corresponding alcohol, that is the alcohol HO—R, which is derived by formal replacement of the alkali metal ion in the alkali metal alkoxide MO—R by a proton.

The 1,1,1-trihaloalkane is reacted with a slurry of the alkali metal alkoxide in the corresponding alcohol. For the purposes of the invention, "slurry" is a suspension of the solid alkali metal alkoxide in the alcohol, only the portion of the alkali metal alkoxide soluble in the amount of alcohol used dissolving in the alcohol and the remainder staying undissolved. The slurry is therefore a suspension of an alkali metal alkoxide in a saturated solution of the alkali metal alkoxide in the corresponding alcohol. The solids content of the slurry is set in such a manner that the viscosity of the slurry is industrially manageable, the slurry can therefore be mixed in the reactors used and—if desired or necessary—is pumpable, but the alcohol content is as low as possible. Excessively high temperature peaks at the points at which reactants are introduced into the reactor must be avoided, since, as a result, the selectivity of the reaction decreases. The upper limit for the viscosity of the entire reaction mixture is therefore given by the ability of the reactor used to mix the components of the reaction mixture sufficiently rapidly.

Generally, use is made of a slurry having a weight ratio of solid to dissolved alkali metal alkoxide of at least 0.4, preferably this ratio is at least 0.7, and particularly preferably at least 0.9. The weight ratio is generally at most 3, preferably at most 2 and in particular, at most 1.5.

Suitable reactors for carrying out the process according to the invention are known to those skilled in the art. Use is made of a reactor which is able to mix the viscous reaction mixture thoroughly. Preference is given to reactors which can mix thoroughly the solids or a slurry having a high solids content rapidly with the liquid components, for example blade driers, kneaders or Discotherm reactors. A further requirement of the reactor is being able to dry readily the alkali metal halide present at the end of the reaction, that is being able to remove the volatile components of the reaction mixture as completely as possible. The reactor is therefore preferably heatable.

Furthermore, the reactor must be provided with a condenser, for example an attached evaporative condenser, an external or internal heat exchanger, in order to be able to remove the heat of reaction formed in the reaction.

Preferably, a blade drier having an evaporative cooler ("reflux condenser") is used as reactor. In a combination of this type, the heat produced in the reactor is removed by evaporating the solvent and/or product from the reactor. The vapors are recondensed at a heat exchanger, the reflux condenser, and are usually recirculated to the reactor, or worked up, for example by isolating the product.

The slurry is brought to reaction with the 1,1,1-trihaloalkane. In this reaction the orthoester and the alkali metal halide are produced. The orthoester, together with the alcohol present in the slurry, is separated off from the alkali metal halide, for example by filtration or evaporation, and then the orthoester is distilled off from the alcohol. The reaction can be carried out continuously or batchwise.

In a preferred batchwise procedure, the slurry is prepared in a blade drier by stirring solid alkali metal alkoxide in the blade drier and metering in the desired amount of alcohol. The heat of solution released is conducted away here by evaporative cooling, the vapors are condensed in an evaporative condenser and the condensate is recirculated to the blade drier. Customarily, slurry preparation with customary sizes of blade driers, customary evaporative condensers and batch sizes determined by these lasts for from 5 minutes to one hour.

The slurry is then reacted with 1,1,1-trihaloalkane. In a batchwise operation, this process step is expediently performed in the same reactor as the slurry preparation, but in principle separate reactors can also be used. Intermediate cooling of the boiling slurry is not necessary, but can be performed.

The 1,1,1-trihaloalkane is metered into the stirred slurry with evaporative cooling and condensate reflux. The addition rate is essentially determined by the cooling rate of the evaporative condenser. The addition, with customary sizes of blade driers, customary evaporative condensers and batch sizes determined by these, generally lasts for from 30 minutes to 2 hours, usually about one hour. Preferably, the production of an excessively high local concentration of the 1,1,1-trihaloalkane is avoided, for this purpose, for example, the 1,1,1-trihaloalkane is either added at a plurality of points distributed over the blade drier or, in a particularly preferred embodiment, is added to the condensate returning from the condenser. Such measures to decrease the local concentration of the 1,1,1-trihaloalkane can also be combined. The molar ratio of alkali metal alkoxide used to 1,1,1-trihaloalkane used is about 3:1. When a stoichiometric deficit of 1,1,1-trihaloalkane is used, the reaction medium stays alkaline continuously, which usually decreases the requirements for corrosion resistance of steels which come into contact with the reaction medium, and therefore frequently makes possible the use of cheaper steels as plant materials. When a stoichiometric excess of 1,1,1,-trihaloalkane is used, in the resultant by-product alkali metal halide, only very small amounts of unreacted alkali metal alkoxide remain, which facilitates its disposal. Whether a stoichiometric excess or deficit of 1,1,1,-trihaloalkane is used or whether this is used as far as possible stoichiometrically, is therefore a parameter to be optimized on the basis of the actual circumstances, such as, for example, the plant materials used, the existing technical possibilities for separating off and purifying unreacted starting materials and the possibilities for disposing the residues. Preferably, at most 1.1 mol of 1,1,1,-trihaloalkane are used per 3 mol of alkali metal alkoxide, particularly preferably at most 0.99 mol. Preferably, at least 0.95 mol of 1,1,1,-trihaloalkane is used per 3 mol of alkali metal alkoxide, particularly preferably at least 0.97 mol.

The reaction is generally carried out at atmospheric pressure at the reaction mixture boiling point which establishes itself. It is equally possible to carry out the reaction under pressure, for example at a pressure of at most 10 bar, preferably at most 5 bar, the boiling point correspondingly increasing. Application of pressure generally makes possible higher space-time yields, since the reaction temperature and thus the degree of conversion increase. However, excessively high reaction temperatures can lead to decreased selectivities, so that the reaction pressure is ultimately selected in the individual case according to economic considerations on the basis of the capacities of the synthetic and work-up parts of the plant.

After all of the 1,1,1,-trihaloalkane has been added, the reaction mixture is preferably allowed to react further for some time with evaporative cooling. The post-reaction period, for customary batch sizes, is for from 5 minutes to 5 hours, preferably for from 15 minutes to 90 minutes.

The volatile components of the reaction mixture are then separated off from the solid components. Preferably, for this purpose, the volatile components are evaporated off by not returning the condensate produced in the evaporative condenser to the reactor, but collecting it in a further vessel. Condensate from a plurality of reactors can also be collected in this vessel. The volatile components are preferably evaporated off at atmospheric pressure or reduced pressure. For complete removal of the volatile components from the reactor, it is advantageous to heat its inner wall, towards the end of the evaporation, to a temperature of at least 20° C. above the boiling point of the reaction mixture, preferably at least 50° C. above this temperature. Generally, it is sufficient for this purpose, to heat the reactor inner wall to at most 150° C. above the boiling point of the reaction mixture, preferably, a temperature of no more than 100° C. above this boiling point is set. This temperature is maintained here until the alkali metal halide which remains as by-product in the reactor is essentially dry. With customary batch sizes, a time in the range from one hour to 10 hours is usually sufficient for this purpose, generally a time from two hours to 4 hours. The dried salt is then removed from the reactor.

The condensate collected, which essentially comprises the orthoester and the alcohol used for slurrying, is then separated into its constituents. Preferably, this is performed by distillation in a known manner. The product of value, the orthoester, is taken off at a commercially conventional purity, for example at a purity of from 99.6% to 99.9% by weight. The distillation is conveniently carried out for this purpose in such a manner that the alcohol distilled off as low-boiler fraction at the top of the distillation tower comprises at least 0.5% by weight, but usually at least 3% by weight, preferably at least 19% by weight, and particularly preferably at least 25% by weight of orthoester. For efficiency reasons, it is expedient to limit the orthoester content of the alcohol distilled off to at most 40% by weight, preferably at most 30% by weight of orthoester.

The principally alcohol-containing low-boiler fraction is preferably reused for slurrying alkali metal alkoxide. To avoid the accumulation of by-products, a portion of this low-boiler fraction is discharged and discarded. This portion is generally at least 2% by weight, preferably at least 5% by weight, and generally at most 20% by weight, preferably at most 10% by weight.

This process can likewise be carried out continuously. For this purpose, it is generally advantageous to perform the slurry preparation and the reaction of the slurry with 1,1,1,-trihaloalkane in separate reactors.

EXAMPLE 108 kg of solid sodium methoxide were charged into a 300 l capacity blade drier equipped with a reflux condenser. With the mixer running, in the course of 20 minutes, 126 kg of methanol were pumped in, the drier contents heating to 82° C., vaporizing methanol condensing in the reflux condenser and running back into the drier. The ratio of solid to dissolved sodium methoxide in the slurry was around 1. Then, in the course of 90 minutes, a total of 77.1 kg of chloroform was added via two separate metering points at atmospheric pressure, the heat of reaction being removed by evaporative cooling. The condensate produced in the reflux condenser ran back into the blade drier. Towards the end of the chloroform addition, the drier was heated to 120° C. and the mixture was kept under reflux for a further 45 minutes. The condensate produced in the reflux condenser was then no longer recirculated to the drier, but passed to a collection vessel. The drier, toward the end of this evaporation process, was heated to 180° C., and after a further 90 minutes the resultant sodium chloride was dried to the extent that it could be discharged from the drier without lump formation.

The condensate collected in the collection vessel comprised 34% by weight of TMOF. It was continuously introduced into a distillation tower having 30 theoretical plates at the height of the 16th theoretical plate. The tower was operated at atmospheric pressure. At a reflux ratio of 1.7, gaseous TMOF was taken off via a side stream take off above the column bottom and condensed. The TMOF condensate had a purity of at least 99.8% by weight. At the top of the tower, a low-boiler fraction was obtained, which fraction consisted of around 90% by weight of methanol, around 5% by weight of TMOF, around 1.5% by weight of chloroform and around 2% by weight of low-boiling minor components. This low-boiler fraction was reused for slurrying sodium methoxide in further batches. Overall, in this manner 6 batches were prepared one after the other. The purity of the TMOF produced was always at least 99.8% by weight. The low-boiler fraction obtained in the last batch consisted of around 90% by weight of methanol, around 6.5% by weight of TMOF, around 1.5% by weight of chloroform and around 2% by weight of low-boiling minor components. Per batch, around 66 kg of TMOF were obtained, which corresponds to a yield of around 93 mol %, based on sodium methoxide used.

Comparative Example 180 kg of a 30% strength by weight solution of sodium methoxide in methanol were charged into a 300 l capacity blade drier equipped with a reflux condenser. As a result, the fill level in the reactor was just as high as in the procedure described in the example above. With the mixer running, the solution was heated to 80° C., vaporizing methanol condensing in the reflux condenser and running back into the drier. Then, in the course of 90 minutes, a total of 39.0 kg of chloroform was added at atmospheric pressure via two separate metering points, the heat of reaction being removed by evaporative cooling. The condensate produced in the reflux condenser ran back into the blade drier. After completion of the addition of chloroform, the mixture was kept under reflux for a further 45 minutes. The condensate produced in the reflux condenser was then no longer recirculated to the drier, but passed to a collection vessel. The drier, toward the end of this evaporation process, was heated to 180° C., and after a further 90 minutes the resultant sodium chloride was dried to the extent that it could be discharged from the drier without lump formation.

The condensate collected in the collection vessel comprised 19.8% by weight of TMOF. It was continuously passed into a distillation tower having 70 theoretical plates at the height of the 36th theoretical plate. The tower was operated at atmospheric pressure. At a reflux ratio of 8, gaseous TMOF was taken off via a side stream take off in the stripping section of the tower and condensed. The TMOF condensate had a purity of at least 99.7% by weight. At the top of the tower, a low-boiler fraction was isolated. This low-boiler fraction, to separate off methanol from other low-boiling components, was passed into a further tower having 40 theoretical plates, at the height of the 35th theoretical plate. The tower was operated at atmospheric pressure. At a reflux ratio of 80, methanol, which comprises less than 1 ppm of chloroform and less than 1000 ppm of TMOF, was taken off at the bottom. Overhead, a fraction consisting of around 60% by weight of methanol and 40% by weight of other low-boiling components was isolated. Overall, 33.9 kg of TMOF was isolated, which corresponds to a yield of around 96 mol %, based on sodium methoxide used.

The example and the comparative example show that the process according to the invention makes possible a yield which corresponds to that in processes customary industrially, but with much less separation effort and thus energy consumption and with substantially higher space-time yield.

We claim:

1. In the process for preparing orthoesters by reacting 1,1,1-trihaloalkanes with alkali metal alkoxides in the presence of the corresponding alcohol, the improvement comprising using a slurry of the alkali metal alkoxide in the corresponding alcohol.

2. The process of claim 1, wherein a slurry of sodium methoxide in methanol is used.

3. The process of claim 1, wherein a slurry of sodium ethoxide in ethanol is used.

4. The process of claim 1, wherein use is made of a slurry having a weight ratio of solid to dissolved alkali metal alkoxide of at least 0.4.

5. The process of claim 4, wherein use is made of a slurry having a weight ratio of solid to dissolved alkali metal alkoxide of at most 3.

6. The process of claim 1, wherein at most 1.1 mol of 1,1,1-trihaloalkane is used per 3 mol of alkali metal alkoxide.

7. The process of claim 1, wherein the reaction is carried out under at least atmospheric pressure and at most 10 bar superatmospheric pressure.

8. The process of claim 1, wherein the product is isolated by distillation which produces an essentially alcohol-containing fraction which, in addition, comprises from 0.5 to 40% by weight of orthoesters.

9. The process of claim 8, wherein use is made of the essentially alcohol-containing fraction for slurrying alkali metal alkoxide.

* * * * *